(12) United States Patent
Chen et al.

(10) Patent No.: US 12,239,331 B2
(45) Date of Patent: Mar. 4, 2025

(54) THERAPEUTIC ULTRASONIC DEVICE AND THE USE THEREOF

(71) Applicant: NATIONAL HEALTH RESEARCH INSTITUTES, Zhunan Township, Miaoli County (TW)

(72) Inventors: Gin-Shin Chen, Zhunan Township, Miaoli County (TW); Li-Chen Chiu, Zhunan Township, Miaoli County (TW); Jiun-Jung Chen, Zhunan Township, Miaoli County (TW); Feng-Huei Lin, Zhunan Township, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 1109 days.

(21) Appl. No.: 16/960,714

(22) PCT Filed: Jan. 8, 2018

(86) PCT No.: PCT/US2018/012778
§ 371 (c)(1),
(2) Date: Jul. 8, 2020

(87) PCT Pub. No.: WO2019/135774
PCT Pub. Date: Jul. 11, 2019

(65) Prior Publication Data
US 2020/0330114 A1    Oct. 22, 2020

(51) Int. Cl.
*A61N 7/02*     (2006.01)
*A61B 17/22*    (2006.01)
(Continued)

(52) U.S. Cl.
CPC ........ *A61B 17/22012* (2013.01); *A61N 7/02* (2013.01); *A61B 2017/0011* (2013.01);
(Continued)

(58) Field of Classification Search
CPC ...... A61B 17/22012; A61B 2017/0011; A61B 2017/00796; A61B 2018/00333;
(Continued)

(56) References Cited

U.S. PATENT DOCUMENTS

| 2008/0200813 | A1* | 8/2008 | Quistgaard | A61B 8/4483 600/459 |
| 2013/0211436 | A1* | 8/2013 | Larson | A61N 7/022 606/169 |
| 2014/0024923 | A1* | 1/2014 | Chapelon | A61B 5/0036 600/407 |

FOREIGN PATENT DOCUMENTS

DE    102005012655 A1 *  9/2006  ......... A61B 5/6843

OTHER PUBLICATIONS

International Preliminary Report on Patentability and Written Opinion issued in corresponding International application No. PCT/US2018/012778 on Jul. 14, 2020.

* cited by examiner

*Primary Examiner* — Michael F Peffley
*Assistant Examiner* — Samantha M Good
(74) *Attorney, Agent, or Firm* — Muncy, Geissler, Olds & Lowe, P.C.

(57) ABSTRACT

The present invention discloses an therapeutic ultrasonic device consisting of at least one arc ultrasonic transducer that can be assembled. The arc ultrasonic transducer comprises a protruding part, a concave part and a plurality of piezoelectric vibrating parts. The protruding part and the concave part are disposed at two ends of the arc ultrasonic transducer respectively, and the piezoelectric vibrating parts are disposed at the inner arc face of the arc ultrasonic transducer. Various numbers of arc ultrasonic transducers can be used in assembled structure or non-assembled structure according to different body size and focal zones of
(Continued)

various target tissue. Thus the therapeutic ultrasonic device of the present invention is widely used in treatment of various indications.

10 Claims, 15 Drawing Sheets

(51) Int. Cl.
*A61B 18/00* (2006.01)
*A61B 17/00* (2006.01)
*A61N 7/00* (2006.01)
(52) U.S. Cl.
CPC ............... *A61B 2017/00796* (2013.01); *A61B 2018/00333* (2013.01); *A61B 2018/00446* (2013.01); *A61B 2018/00577* (2013.01); *A61N 2007/0004* (2013.01); *A61N 2007/0065* (2013.01); *A61N 2007/0082* (2013.01)
(58) Field of Classification Search
CPC ............ A61B 2018/00446; A61N 7/02; A61N 2007/0004; A61N 2007/0065; A61N 2007/0082
See application file for complete search history.

THERAPEUTIC ULTRASONIC DEVICE AND THE USE THEREOF

FIELD OF THE INVENTION

The present invention relates to an ultrasonic device, especially refers to the therapeutic ultrasonic device that can produce high intensity focused ultrasound (HIFU) or low intensity focused ultrasound (LOFU) with different focal zones into different kinds of biological tissue to destroy cells or stimulate cells.

BACKGROUND OF THE INVENTION

Focused ultrasound represents that ultrasound beams converge on a small region called as focal zone by a geometric concave or tuning electronic phase of the ultrasonic transducer. A focused ultrasound transducer can produce high intensity focused ultrasound (HIFU) or low intensity focused ultrasound (LOFU) in accordance with the input power. Typically, HIFU causes high-temperature ablation or mechanical cavitation on the target tissue as LOFU results in mild-temperature hyperthermia or pressure on the target tissue for disrupting or stimulating the tissue. For safety, treating diseases with HIFU or LOFU is usually accomplished with real-time imaging via magnetic resonance imaging (MRI) or ultrasound imaging.

Treating biological tissue with HIFU or LOFU is a non-invasively therapeutic method. It has advantages of no incision on the tissue, localized treatment with the tissue, low side effects, no anesthesia requirement, no hospitalization requirement and a short recovery period, therefore, it is a promising modality in clinical applications. Furthermore, the treating process with high intensity focused ultrasound is not limited with the size and shape of the solid tumors, so worldwide related research institutions propose different treating methods using high intensity focused ultrasound for cancers in succession. So far, Uterine fibroids, pain induced by metastasized bone cancer, prostate cancers and essential tremor have been approved by Food and Drug Administration (FDA) of the United States in 2014, 2012, 2015 and 2016 respectively, and many research units are striving to establish and improve the treating method with HIFU or LOFU for brain tumor, Alzheimer's disease, stroke, brain trauma, breast tumor, liver tumor, pancreatic cancer and hypertension.

The ultrasonic transducer is used as a converter between the electrical signals and ultrasounds, and it's a key element in the treating systems using high intensity focused ultrasound or LOFU. It can be classify into five kinds of ultrasonic transducers according to the working principles and materials, including piezoelectric transducers, electrostatic transducers (also known as capacitive transducers), magnetic transducers, electromagnetic transducers, and mechanical transducers. Based on the clinical treating experience of prior arts, there are problems to be solved during the treating process. Different tissue are shielded by different parts of body, for example, organs located inside the chest are shielded by sternum and brain tissue is shielded by skull. Besides, the distances from tissue to body surface vary among different tissue. So that the ultrasonic focal zone and treating strength are not consistent when treating high intensity focused ultrasound or LOFU to different tissue. On the other hand, different treating purpose such as destroying cells or stimulating cells also affect the parameters of focused ultrasounds. According to the description of prior arts, high intensity focused ultrasonic treatment using a spherical-bowl ultrasonic transducer on different tissue may lead to skin burn or non-target tissue treatment because its acoustic window (ultrasound transmitting area) on the skin is narrow and acoustic path is perpendicular to non-target tissue. Furthermore, since a single sonication of the bowl focused ultrasound transducer induces a rather small focal zone of mm scale in the target tissue, the treatment time is rather long for the target tissue in cm scale. Developing different-geometry ultrasonic transducers that are specific for different tissue respectively may increase the complexity of clinical operation and the costs of device.

According to the described problems of prior arts, the present invention provides a therapeutic ultrasonic device, which can be widely applied for treating disease and health care prevention on different tissue. The invention decreases the risk of non-target tissue damage and the costs of production and development of ultrasonic transducer, but enhances the treatment efficiency.

SUMMARY OF INVENTION

Accordingly, in one aspect, the present invention relates to an therapeutic ultrasonic device comprising, at least one arc ultrasonic transducer that can be assembled; a protruding tenon part which is disposed at one end of the arc ultrasonic transducer; a concave mortise part which is disposed at another end of the arc ultrasonic transducer; and a plurality of piezoelectric vibrating parts which are disposed at the inner side of the arc of the arc ultrasonic transducer.

In certain embodiments of the present invention, the arc ultrasonic transducer can be assembled into a ring-shaped ultrasonic transducer or an open cylindrical ultrasonic transducer.

In certain embodiments of the present invention, the protruding parts assemble with the concave parts to form the ring-shaped ultrasonic transducer or the cylindrical ultrasonic transducer.

In certain embodiments of the present invention, the arc ultrasonic transducer is a phased array ultrasonic transducer.

In certain embodiments of the present invention, each piezoelectric vibrating part further comprises a piezoelectric sensing element.

In certain embodiments of the present invention, geometric parameters of the arc ultrasonic transducer are radius of curvature R in a range of 5 to 25 cm, aperture diameter D in a range of 10 to 40 cm, and height H in a range of 1 to 3 cm.

In another aspect, the above-mentioned therapeutic ultrasonic device is used for producing thermal effects and/or mechanical effects on biological tissue In certain embodiments, the cylindrical ultrasonic transducer or the arc ultrasonic transducer induces cavitation in the microenvironment of the tissue to produce the mechanical effects.

In certain embodiments, the high-temperature thermal effects on the tissue lead to coagulative necrosis or cell death.

In certain embodiments, the mild-temperature thermal effects and/or the pressure on the biological tissue lead to cell activation, cell differentiation or cell regeneration.

In certain embodiments, when the therapeutic ultrasonic device is used in breast tissue or brain tissue, four arc shaped ultrasonic transducers are assembled into the ring shaped ultrasonic transducer.

DETAILED DESCRIPTION OF THE INVENTION

Focused ultrasound is defined as forming focal zones on target tissue via concentrating multiple beams of ultrasound by geometric principle or electronic operation. According to the prior arts of ultrasonic treating systems using focused ultrasound, there are problems to be solved. One of the problems is that the ultrasonic energy density is high on the skin due to a narrow acoustic window when the target tissue near the skin is treated by using the spherical-bowl focused ultrasound transducer, so that it may cause skin burn. Moreover, the propagation direction of ultrasonic waves emitted by the spherical-bowl focused ultrasound transducer is vertical to the non-target tissue behind the target tissue, leading to unexpected treatment of non-target tissue. In addition, the spherical-bowl focused ultrasound transducer generates a small focal zone to perform "point" treatment, which certainly takes long time to treat a large target tissue. Developing individual ultrasonic devices for a variety of different tissue not only increasing the complexity of clinical operation but increasing the costs of the therapeutic ultrasonic devices. Accordingly, the present invention provides a therapeutic ultrasonic device, which comprises one arc ultrasonic transducer or multiple arc ultrasonic transducers that are assembled to be adapted to various body sizes according to the distance from tissue to the body skin and to achieve multiple focal zones concurrently for volumetric treatment in large target tissue or a single focal zone with a wide acoustic window on the skin and with an acoustic path parallel to non-target tissue. So that, the arc ultrasonic transducer with the same geometric characteristics of the therapeutic ultrasonic device can be applied to many kinds of tissue. Besides, the present invention also relates to the aforementioned therapeutic ultrasonic device for use in producing thermal effects and/or mechanical effects on the tissue. Hereinafter, the device and the use thereof of the present invention will be described.

Figure 1:
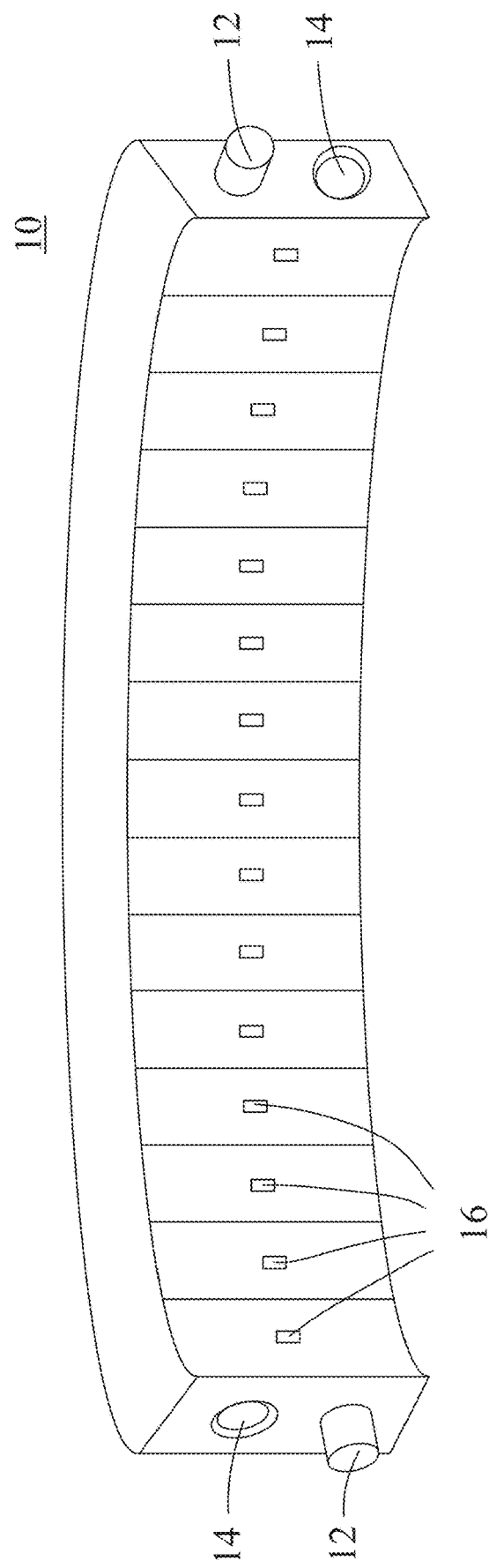
FIG. 1 shows the first embodiment of the arc ultrasonic transducer of the present invention.

Please refers to FIG. 1, it shows the first embodiment of the arc ultrasonic transducer of the present invention. According to the figure, arc ultrasonic transducer 10 includes protruding part 12, concave part 14 and piezoelectric parts 16, wherein the protruding part 12 and the concave part 14 are disposed at two ends of the arc ultrasonic transducer 10 respectively, that is, if the protruding part 12 is disposed at one end of the arc ultrasonic transducer 10, the concave part 14 is disposed at the other end of the arc ultrasonic transducer 10. In addition, the piezoelectric parts 16 are disposed at the inner side of the arc of the arc ultrasonic transducer 10.

As the description above, the geometric parameter of the arc ultrasonic transducer are radius of curvature R in range of 5 to 25 cm, aperture diameter D in range of 10 to 40 cm, and height H in range of 1 to 3 cm.

In addition, the protruding part is as a tenon part and used for joining the concave part which is as a mortise part. For further details, the protruding part or the concave part located at a first arc ultrasonic transducer is joined to the concave part or the protruding part located at a second arc ultrasonic transducer to form a ring-shaped ultrasonic transducer or a cylindrical ultrasonic transducer. Because the structure of the arc ultrasonic transducer is symmetrical curved structure, the direction of the arc ultrasonic transducers would not be limited when they are assembled via the protruding part and the concave part. The numbers of the protruding parts and the concave parts are variable according to the size of the arc ultrasonic transducer but not limited to the present embodiment.

Different tissue locate at various sites of the body, so that different tissue are shielded by different body sizes (e.g., skull, extremities, upper trunk or lower trunk) and different biological structures (e.g., head skull, sternum or adipose tissue). Furthermore, different body sizes and different biological structures affect the size of ultrasonic transducer and the operative angle during treating process. For examples, the size of the ultrasonic transducer used for target tissue which are located inside the upper trunk (e.g., liver tissue or breast tissue) is smaller than the ultrasonic transducer used for brain tissue which are located inside the skull. The operating angle of the ultrasonic transducer when treating liver tissue is different from treating breast tissue. Accordingly, the numbers of the arc ultrasonic transducer of the present embodiment is decided according to the body size. In preferred embodiment, one arc ultrasonic transducer is operated individually or two arc ultrasonic transducer are cooperated without being joined to each other. In another preferred embodiment, two or four arc ultrasonic transducers are assembled via the protruding part and the concave part to form the ring-shaped ultrasonic transducer or open cylindrical ultrasonic transducer for surrounding the body region corresponding to the target tissue. So that, the limitations of the prior arts that a single mode ultrasonic transducer could not be used for various tissue are excluded by using the arc ultrasonic transducer of the present invention. The costs of device production and device development are decreased and the complexity of clinical treatment is also decreased.

Owing to the acoustic window of the ring-shaped ultrasonic transducer or two non-assembled arc ultrasonic transducer is wild enough to disperse the energy of ultrasonic beams, skin burn or normal tissue burn caused by accumulating energy are prevented. In some particular embodiments, the ultrasonic beams emitted from the arc ultrasonic transducer or the ring-shaped ultrasonic transducer is parallel to bone tissue, so that bone tissue damages caused by direct irradiation of focused ultrasonic beams or skin and other non-target tissue damages caused by reflection of focused ultrasonic beams as the prior arts will be prevented.

On the other hand, the piezoelectric parts are made of piezoelectric materials. Piezoelectric materials are dielectric materials that are able to convert the mechanical energy to electric energy. Hence, the piezoelectric parts are converters for electrical signals-ultrasonic beams transition that produce piezoelectric effects when receiving electrical signals or ultrasonic beams. In one embodiment of the present invention, the piezoelectric parts are driven individually. When electrical signals with operating frequency are imported to the piezoelectric parts, ultrasonic beams with corresponding frequency will be emitted from the piezoelectric parts. In a preferred embodiment, the operating frequency of the piezoelectric parts range from 0.2 MHz to 4.0 MHz, and the mode for electrical signals is continuous mode, burst mode or pulse mode.

In addition, the piezoelectric parts further include a piezoelectric sensing element respectively. When ultrasonic beams that emitted from each of the piezoelectric parts are delivered to the interface between two tissue with different acoustic impedance, echo signals will be produced and then be detected by the piezoelectric sensing element that embedded in each of the piezoelectric parts. After that, driving phase of each of the piezoelectric parts is adjusted according to a time lag value calculated from the time point of the ultrasonic beams emission to the time point of the echo signals reflection. For further details, adjusting the driving phase of each of the piezoelectric parts will concentrate the ultrasonic beams to form a focal zone, and the focal zone is moved electrically to achieve dynamic focusing and focal steering into target tissue. Besides, the piezoelectric parts are arranged at the inner arc face of the arc ultrasonic transducer, so a single ultrasonic focal zone or multiple ultrasonic focal zones can be generated by regulating the driving phase for small-area tissue (mm-scale) or large-area tissue (cm-scale) respectively. In summary, driving phase parameters of the piezoelectric vibrating parts can be adjusted according to the time lag between the ultrasonic beams emission and echo signals reflection to ensure that the ultrasonic beams is sustained and accurately focused into the target tissue. Not only the non-target tissue burns caused by deviation of the focal zones will be excluded but the efficiency of treatment will be improved by forming multiple ultrasonic focal zones.

When the focal zone of the ultrasonic beams is emitted into the target tissue, microbubbles will be formed in the microenvironment of the tissue and cavitation will be generated by the interaction of the microbubbles with the ultrasonic beams. The microbubbles are exploded by the abrupt difference in ultrasound pressure to destroy cells. The phenomenon is inertial cavitation. On the contrary, the stable cavitation produces periodically oscillating bubbles to stimulate cells.

The thermal effects on the target tissue produced by the focused ultrasonic beams induce tissue ischemia, leading to oxygen and other nutrients cannot be transported to the tissue, or cause protein denaturation, leading to coagulation necrosis, also known as thermal ablation. The thermal effects caused by the focused ultrasonic beams can be divided into high temperature heating and moderate temperature heating. In one embodiment of the present invention, the temperature range of the high temperature heating is between 55° C. and 85° C. and the heating time is between 5 and 10 seconds, preferably, the target tissue can be treated at 60° C. for 6 seconds to destroy the cells. The temperature range of the moderate temperature heating is between 40° C. and 50° C. and the heating time is between 10 and 30 minutes, preferably, the target tissue can be treated at 43° C. for 30 minutes to destroy the cells. Accordingly, high intensity focused ultrasound can be used to eliminate benign cysts or malignant tumors.

On the other hand, treating the target tissue with moderate temperature heating for a short period of time can produce the effects of stimulating the cells of the target tissue, preferably, the target tissue can be treated at 40° C. for 5 minutes to stimulate and activate cells. Accordingly, high intensity focused ultrasound can also be applied to regenerative medicine, disease prevention or tissue health care. The stable cavitation mechanical effects produced on the tissue will induce mechanical agitation, thereby changing the physical properties between cells and facilitating the delivery of the drugs to the target tissue.

Lastly, focused ultrasound driven by pulsed signals can generated localized force or pressure on the target tissue and cells as the stimulus, which cannot induce thermal effects.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever. All publications cited herein are incorporated by reference.

EXAMPLES

Materials and Methods

Fabrication of the Arc Transducer

PZT4 ceramic chips (Ceramic Transducer Design, Taiwan) were used as the material of the piezoelectric elements in one embodiment of the present invention due to its high depoling voltage and low dielectric losses under a high electric drive. Sixteen curved piezoelectric elements with the radius of curvature of 10 cm were sequentially glued to the arc shape acrylic case of 20 cm in diameter by epoxy. The gaps between the piezoelectric elements and acrylic case were sealed by epoxy for waterproof. The 30-AWG coaxial cables (D1370115BT, Wellshow Technology, Taiwan) were used for electrical connection. All the materials used in the arc transducer are non-ferro for MRI compatibility.

Parameters Measurement

The impedance of each piezoelectric element was measured by an impedance analyzer (Impedance Analyzers 6500B, Wayne Kerr Electronics, UK). The matching circuits were designed by the software Smith Chart (Smith V3.10, Bern University of Applied Sciences, Switzerland) to fit the requirements of the impedance phase close to 0°, and the impedance magnitude close to 50Ω at the frequency of 1.0 MHz. The electroacoustic conversion efficiency of the arc transducer was measured by the radiation force balance (RFB-2000, Onda, USA). A 1.5 T MRI system (Symphony, Siemens, Germany) was used to perform the MRI compatibility test of the ring transducer and the temperature measurement.

Geometric Characteristics of Arc Ultrasonic Transducer

The arc transducer is divided by piezoelectric elements of equal size and the number of the piezoelectric element is related to the intensity patterns in the focal plane. The relationship between the phase distribution φi over the N piezoelectric elements and focal intensity patterns is given in Equation (1) derived by Cain and Umemura (Cain, C. A. et al, 1986. 34(5): p. 542-551).

$$\phi_i = mi\frac{2\pi}{N}; \quad \text{Equation (1)}$$

where m and i represent the mode number of focal intensity patterns and the piezoelectric element number, respectively (i=0, 1, 2, . . . , N−1) and 0≤m≤N/2. In other words, m kinds of intensity patterns are generated by at least 2 m elements as the phase supplied to each element is set by following Equation (1).

Ultrasonic intensity patterns in one medium can be obtained by Equation (2) and Equation (3) once the phase of piezoelectric elements is given by Equation (1). Equation Equation (2) is adopted to calculate acoustic pressure in the field of interest under two postulates: plane waves and transverse waves. Equation (2) is derived from the Rayleigh-Sommerfeld integral (Schmerr, L. W., 1998, New York: Plenum Press. xiii, 559 p.).

$$p(x, y, z) = j\rho f \sum_{m'=1}^{M'} \sum_{n'=1}^{N'} \frac{u_{m'n'} e^{j(\phi_{m'n'} - k r_{m'n'})}}{r_{m'n'}} \Delta S_{m'n'}; \quad \text{Equation (2)}$$

where p(x,y,z) is the acoustic pressure at point (x, y, z), rm'n' means the distance between the point (x, y, z) and acoustic source point m'n' with an area of ΔSm'n' at the transducer, ρ is the density of the wave-propagation medium, f is the operation frequency of the transducer, um'n' is the amplitude of complex surface velocity at the point source m'n', k is the wave number, and the transducer is modeled by M' by N' numerical piezoelectric elements in the numerical computation.

$$I = \frac{|p(x, y, z)|^2}{2\rho c}; \quad \text{Equation (3)}$$

where I is the acoustic intensity (W/cm2) at point (x, y, z), and c is the acoustic speed in the medium (m/s).

Operation of Arc Ultrasonic Transducer or Ring-Shaped Ultrasonic Transducer

In all ablation experiments of the present invention, the arc transducer or the ring-shaped ultrasonic transducer are driven by the power amplifier (Phased array generator 500-013, Advanced Surgical System, MA, USA).

Phantom Ablation Experiments

Figure 2A:
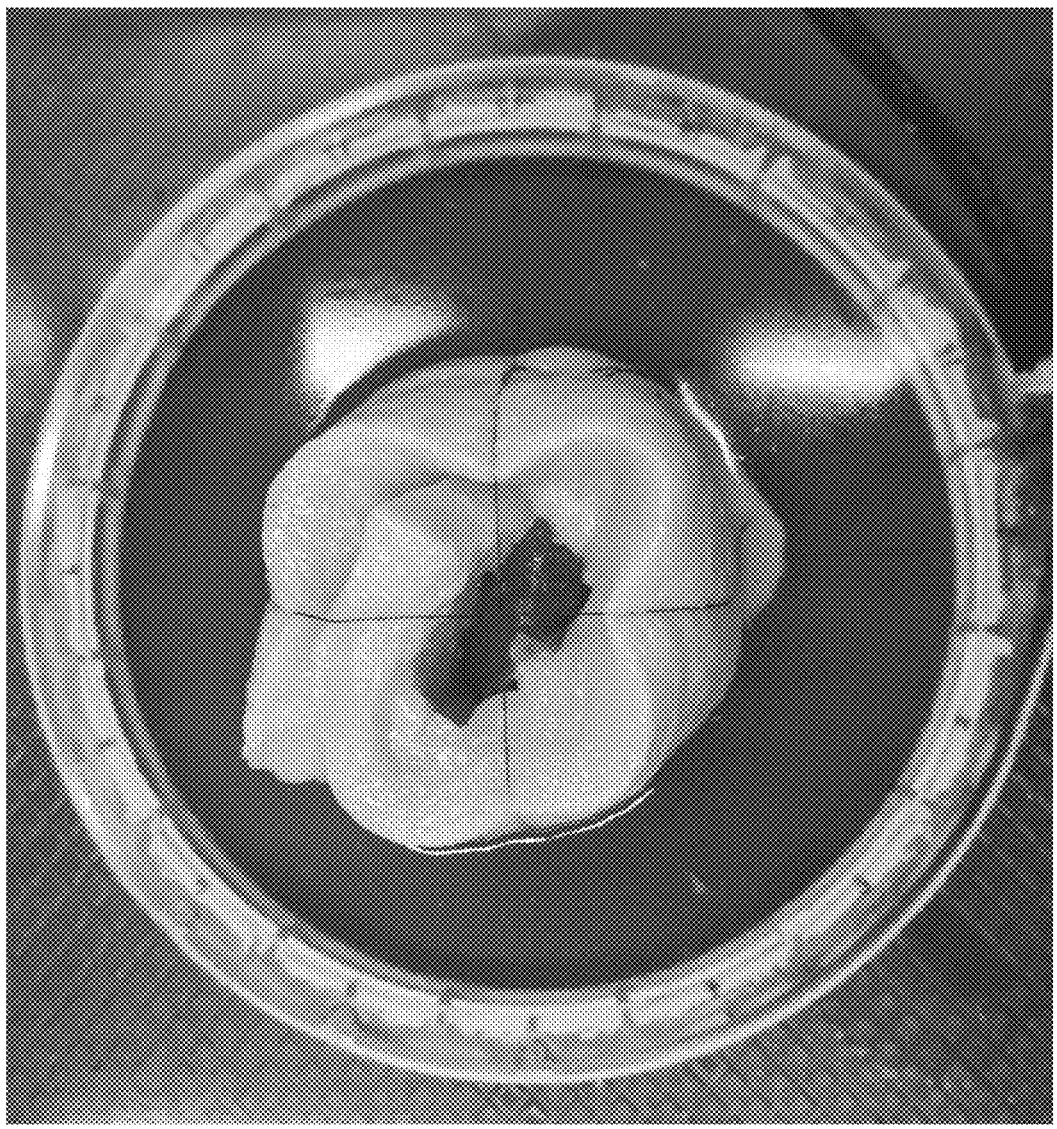
FIG. 2A-2B show the material of ablation experiment.
Figure 2B:
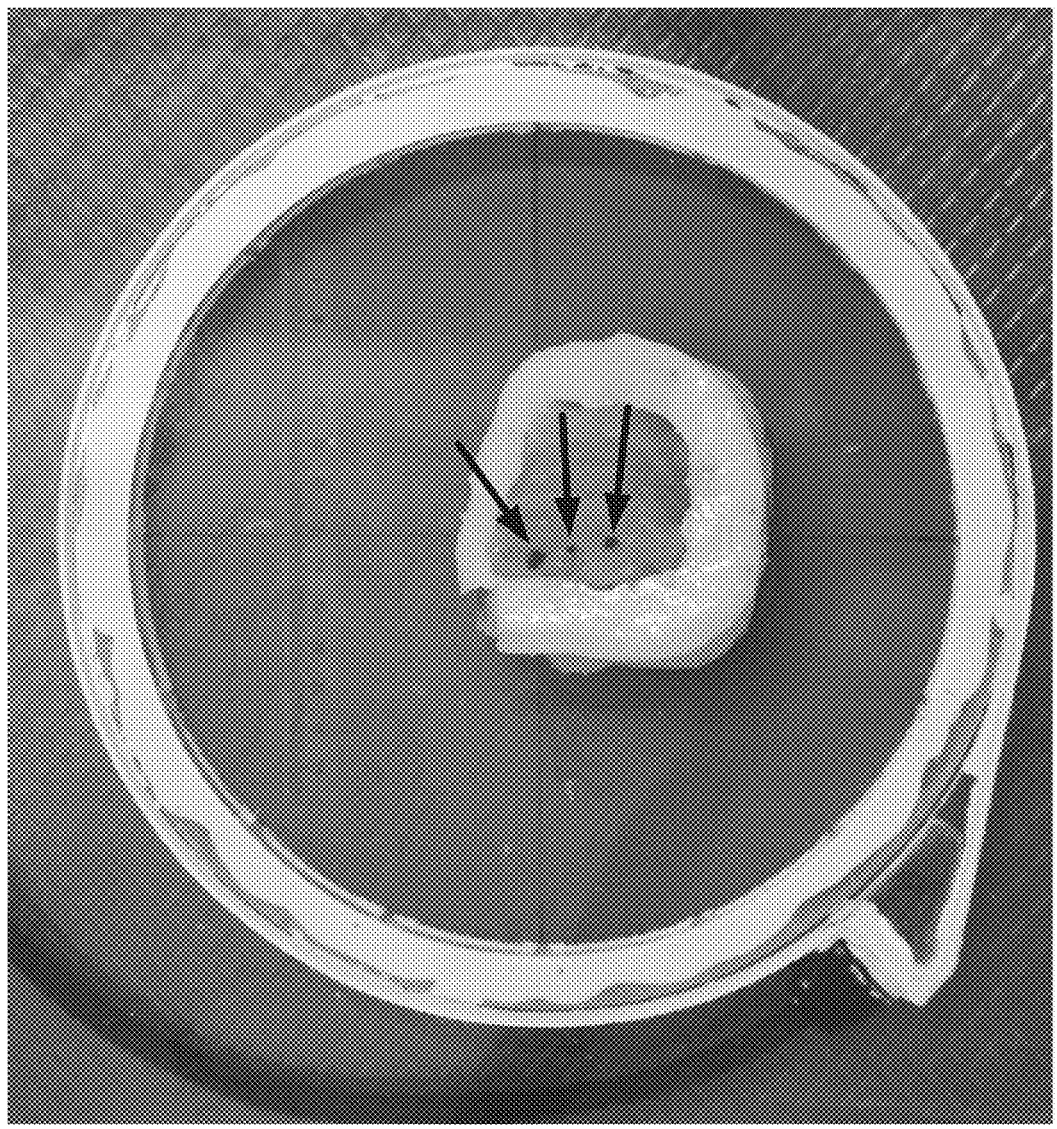

For each ablation experiment in the embodiments of the present invention, a quasi-cuboidal porcine muscle (4×4×4 cm) was used and surrounded with porcine subcutaneous fat in 25° C. degassed water as shown in FIG. 2A. The muscle sample was located at the center of the ring transducer and the sample number was three for a set of HIFU parameters. The electrical power and time of HIFU sonication were in a range of 370 to 516 W and 3 to 5 seconds. For the skin burn issue, three specific points of a porcine muscle (5×5×4 cm) surrounded with fat was ablated. The distance between the desirable ablation points and the inner boundary of fat was 1, 5 and 10 mm, respectively as shown in FIG. 2B by the arrows. The ablation point was manually moved to align the center of the ring transducer. The mode 0 was used for all experiments. After the ablation, the muscle tissues were cut in slices transversely for lesion observation.

The threshold of HIFU dose to form the lesion was searched by adjusting the electrical power and time. Furthermore, the ablation process was videotaped to estimate the ablated area using the software Image J (1.50i, National Institute of Health, US).

Example 1. Simulated Intensity Field of the Ring-Shaped Transducer

For the arc transducer that composed of 16 piezoelectric elements in the present embodiment, there would be 9 sets of phase to produce corresponding 9 modes of intensity pattern in accordance to the Equation (1). FIGS. 3A-3F show simulated intensity contours of the mode 0 and the mode 8. For the other modes that are not shown in figures, the focal zone of the modes 1-3 is not a solid ellipsoid and the focal pattern of the modes 4-7 is similar to the mode 8 but disorderly. The region of −6 dB peak intensity is defined as focal zone.

Figure 3A:
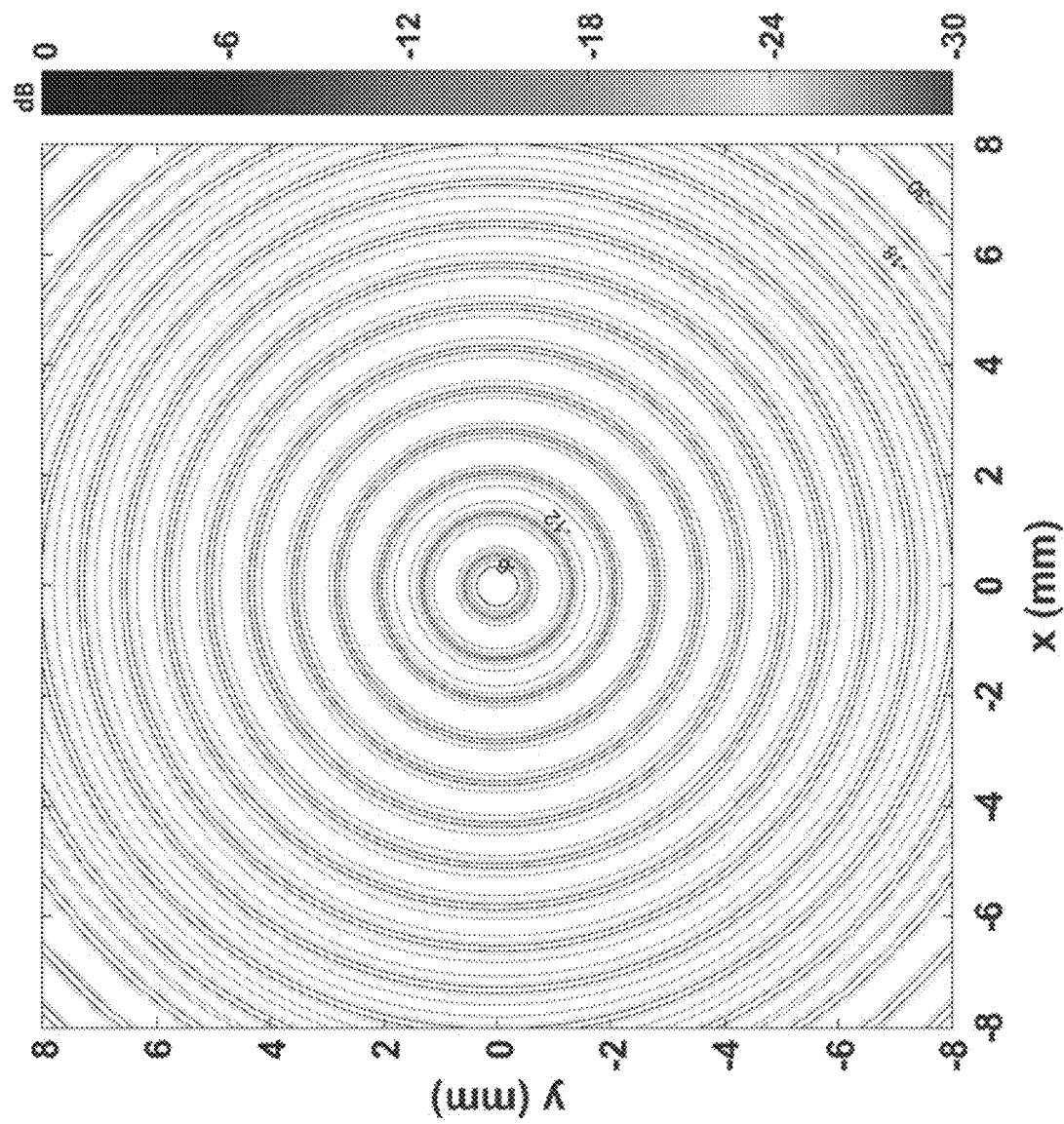
FIG. 3A-3F show simulated intensity contours.
Figure 3B:
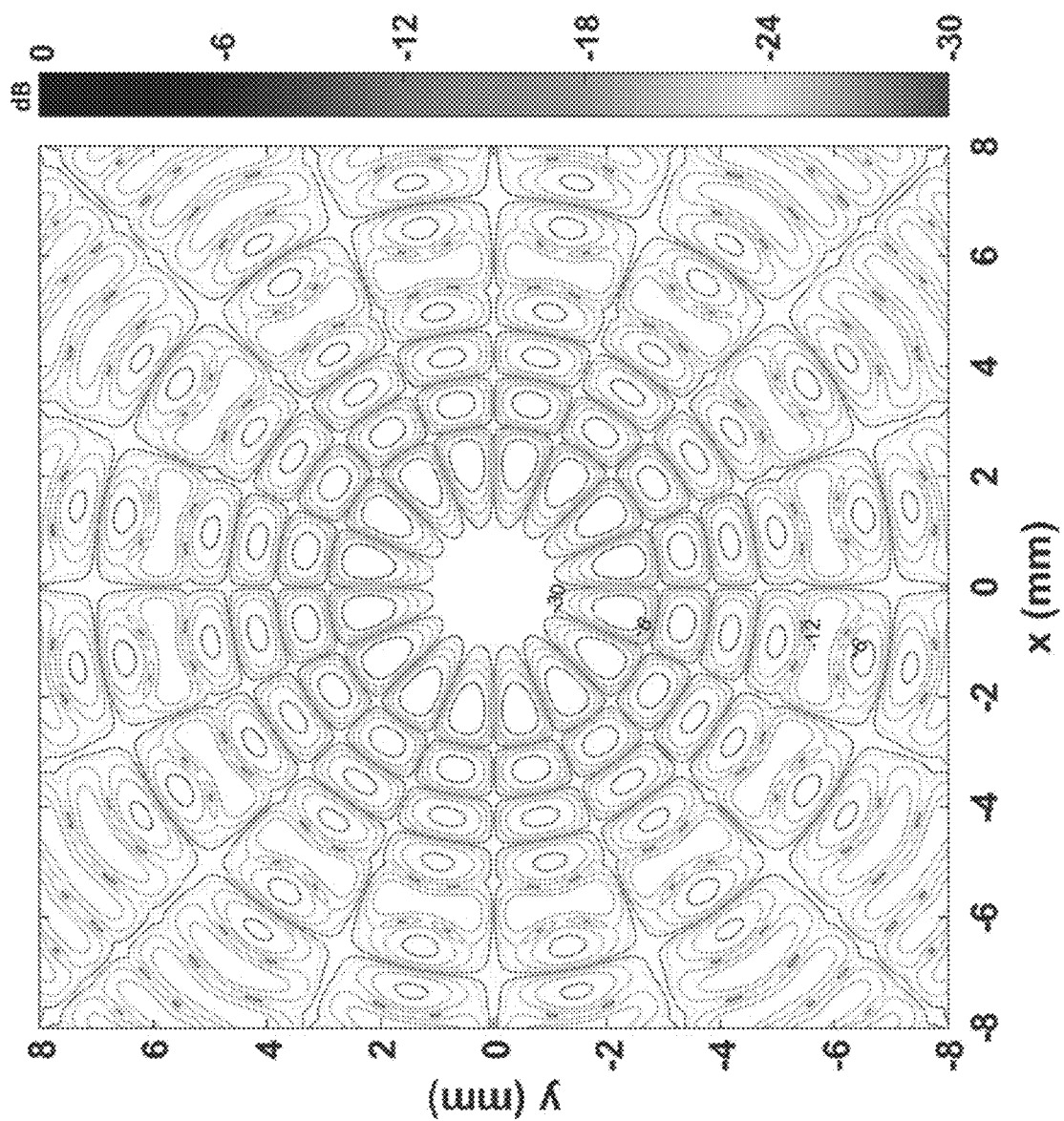
Figure 3C:
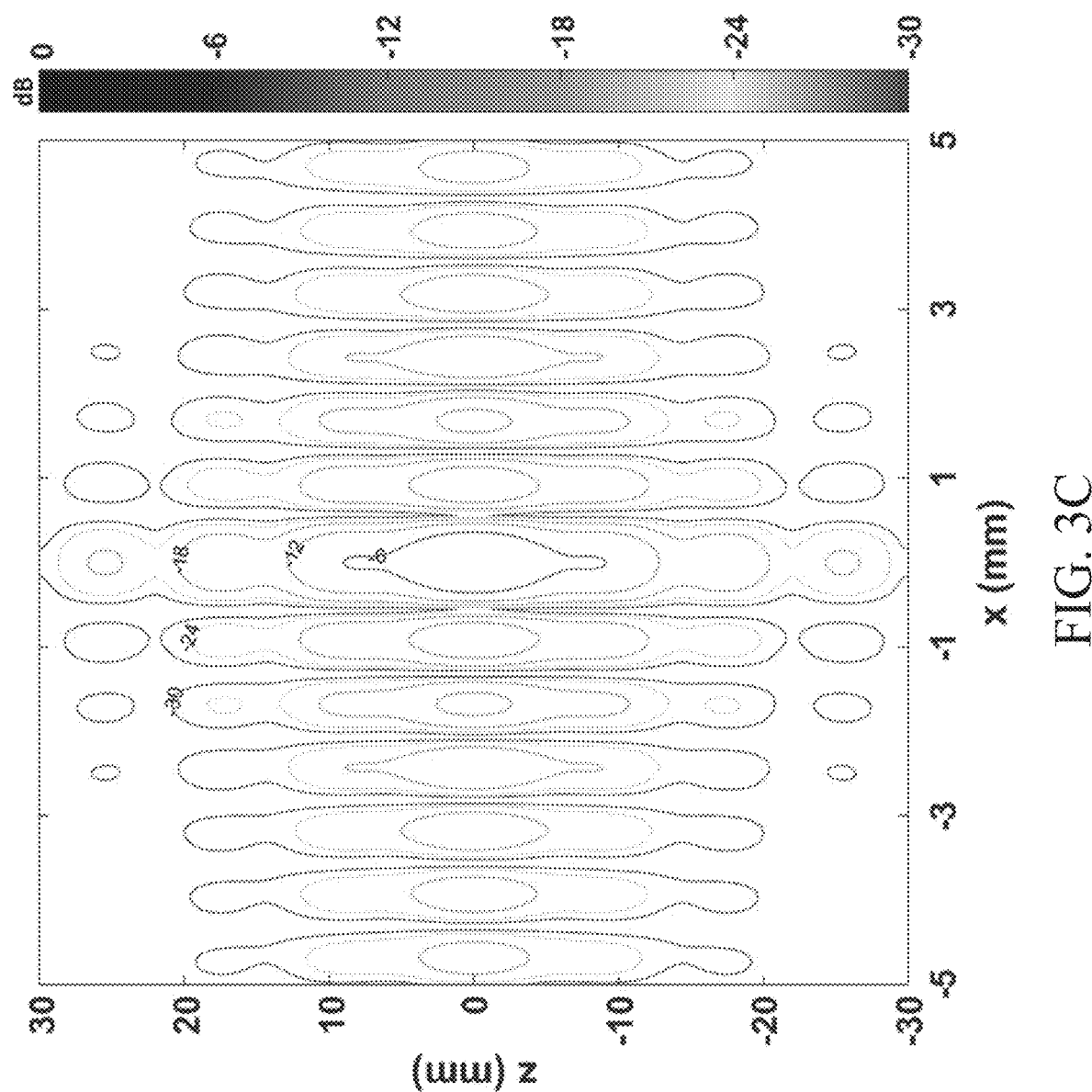
Figure 3D:
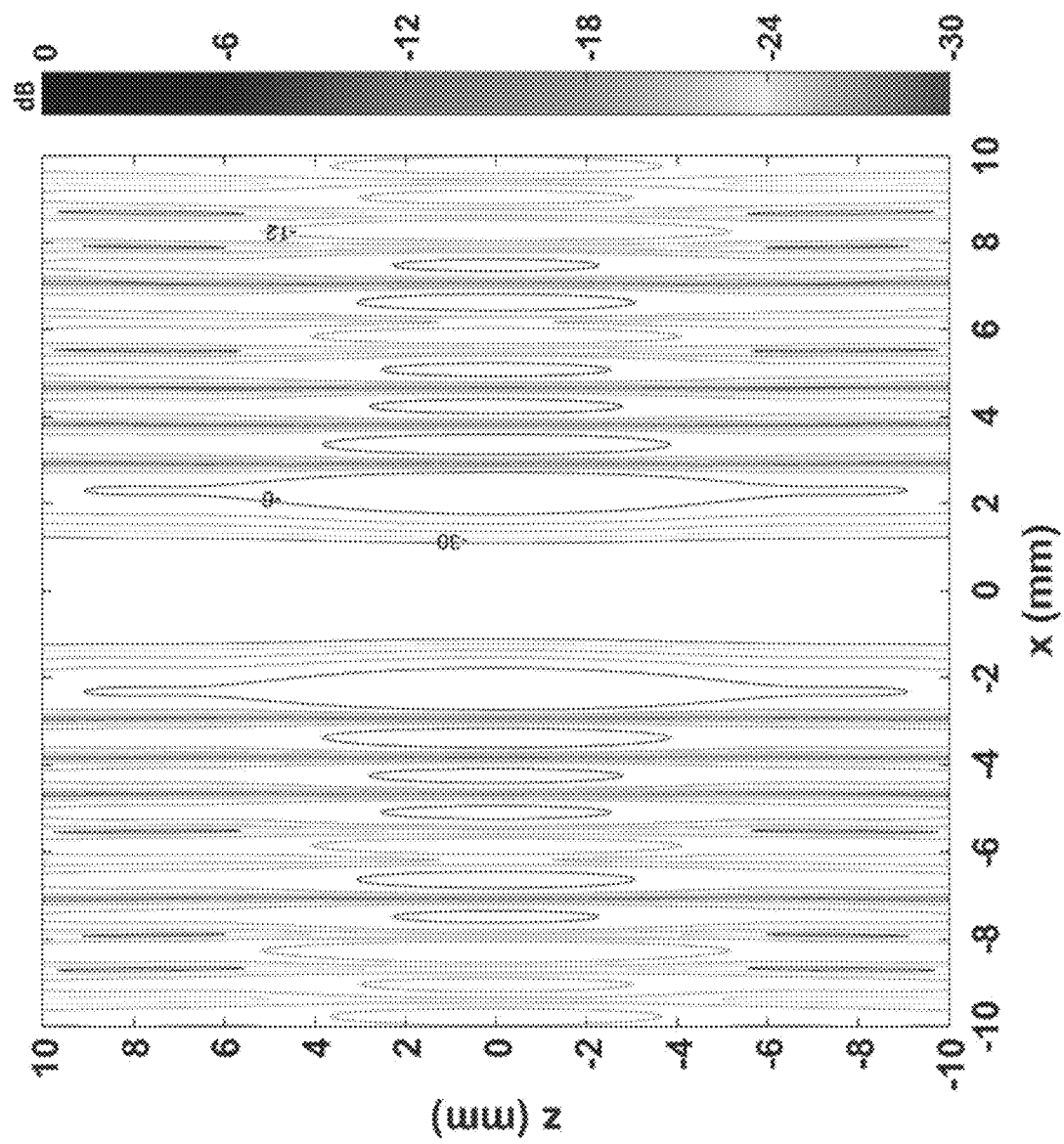
Figure 3E:
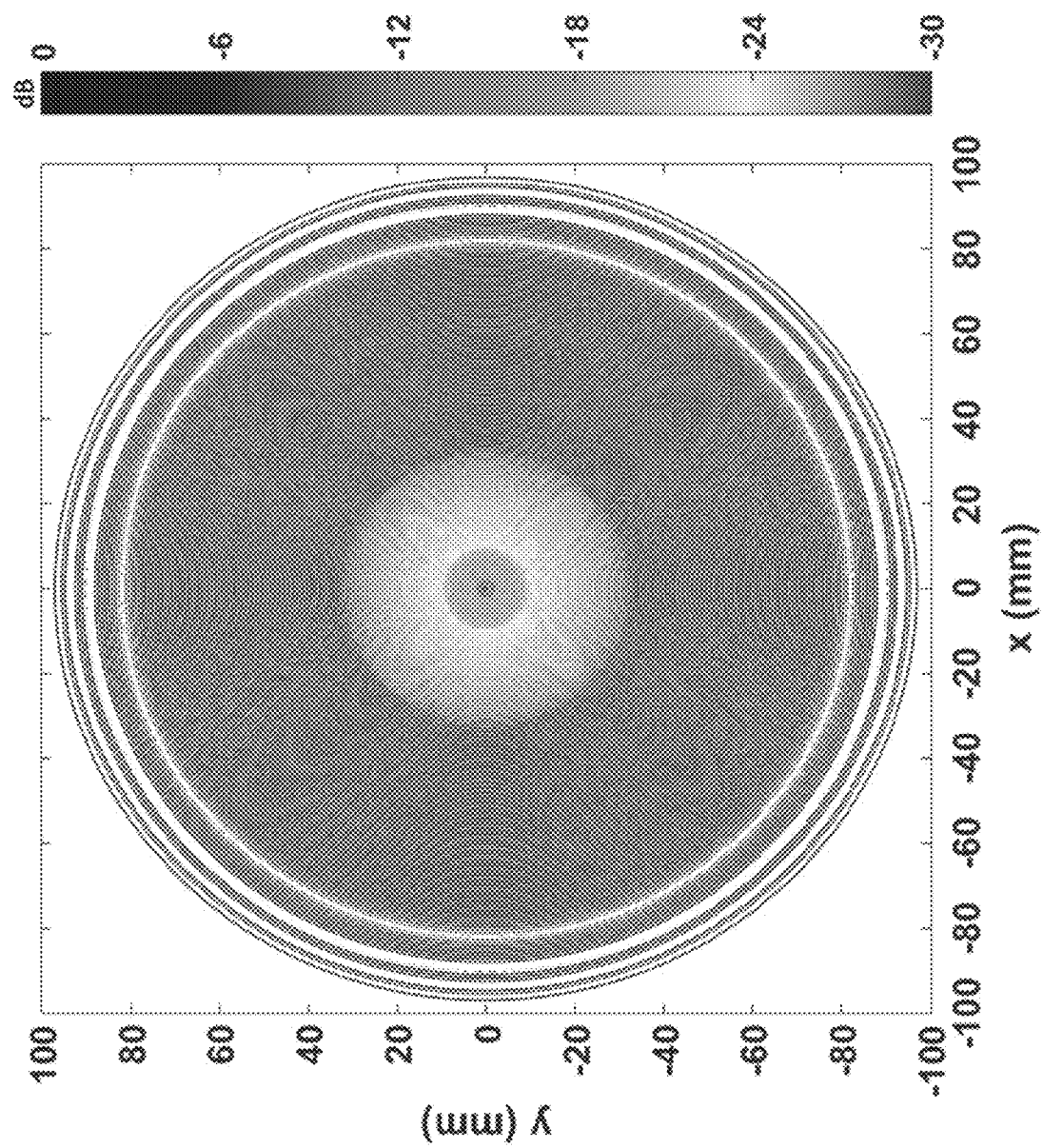
Figure 3F:
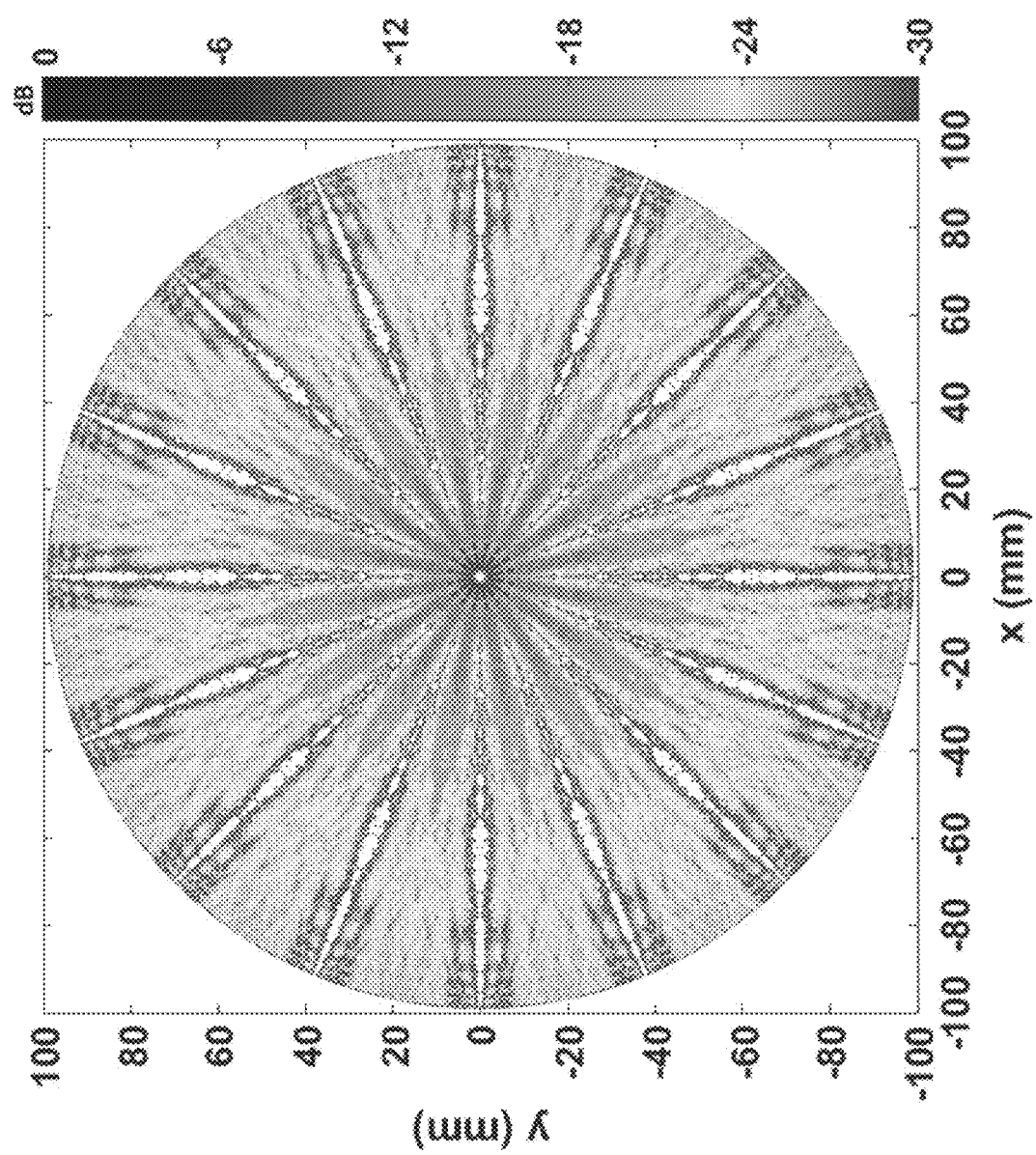

For the mode 0, the phase of each piezoelectric element is zero and the focal zone is a solid ellipsoid with the diameter of 0.7 mm and the length of 12.5 mm (FIG. 3C) at the center of the ring-shaped transducer that are assembled using the arc transducer. For the mode 8, the phase of 16 elements is 0, 180o, 0, 180o, 0, 180o, 0, 180o, 0, 180o, 0, 180o, 0, 180o, 0, 180o, respectively and multiple foci are simultaneously generated and deployed along 6 annuli (FIG. 3B). The 16 foci are distributed symmetrically in each annulus. The inner diameter of the 1st annulus is 3.5 mm and the outer diameter of the 4th annulus is 12.9 mm. Moreover, the inner diameter of the 5th annulus is 13.6 mm and the outer diameter of the 6th annulus is 15.2 mm. Each focal zone is like a solid ellipsoid (FIG. 3D) and the dimensions of the foci from the 1st to 6th annulus are 1.0 mm in diameter×12.5 mm in length, 0.5×7.7 mm, 0.3×5.6 mm, 0.3×5.1 mm, 0.4×6.1 mm and 0.3×4.6 mm in turn. The annular center is the center of the ring-shaped transducer. FIGS. 3E and 3F illustrate the whole intensity field of the mode 0 and mode 8 on the central xy plane. The grating lobes or other focusing didn't occur outside the central focal region of the transducer.

Example 2. Lesion Formation by HIFU Via Ring-Shaped Transducer

Figure 4:
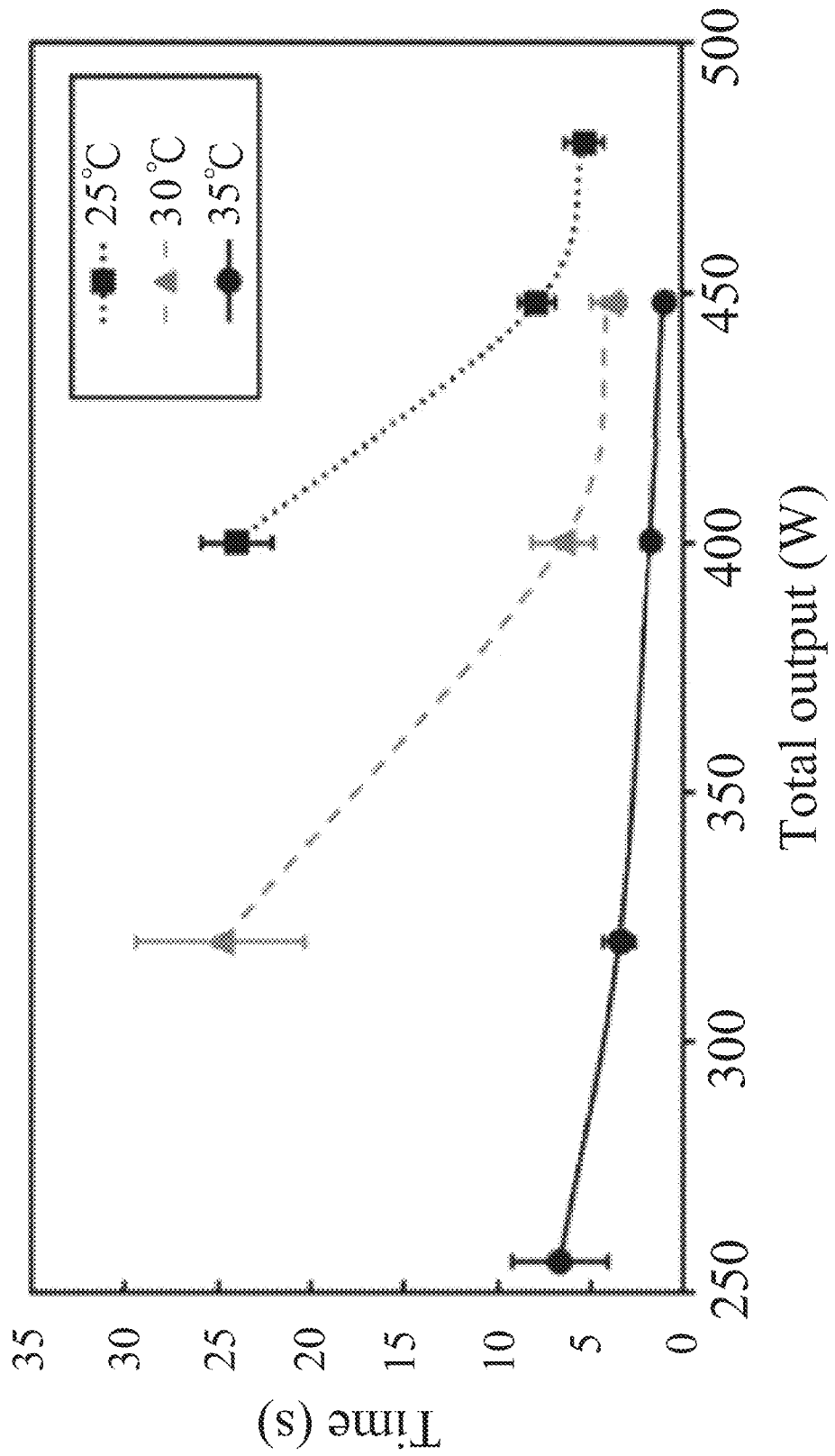
FIG. 4 shows the correlation between the initial temperature of the phantom and the time to see the lesions.

FIG. 4 shows the correlation between the phantom temperature and the time to see the lesion as the HIFU mode is 0. For the phantom temperature of 25° C., the HIFU dose to form a white lesion is 400 W/24.0 seconds, 448 W/7.8 seconds and 480 W/5.3 seconds, but no lesion is observed after the sonication of 256 W or 320 W for 60 seconds. When the phantom temperature is increased by 5° C., the HIFU dose to form the lesion is decreased to be 320 W/24.8 seconds, 400 W/6.5 seconds and 448 W/4.0 seconds, but there is still no lesion after the sonication of 256 W/60 seconds. Further increasing the phantom temperature to 35° C. resulted in the lower HIFU dose to from the lesion such as 256 W/6.7 seconds, 320 W/3.5 seconds and 420 W/1.8 seconds.

Example 3. Ex Vivo Ablation by HIFU Via Ring-Shaped Transducer

Figure 5:
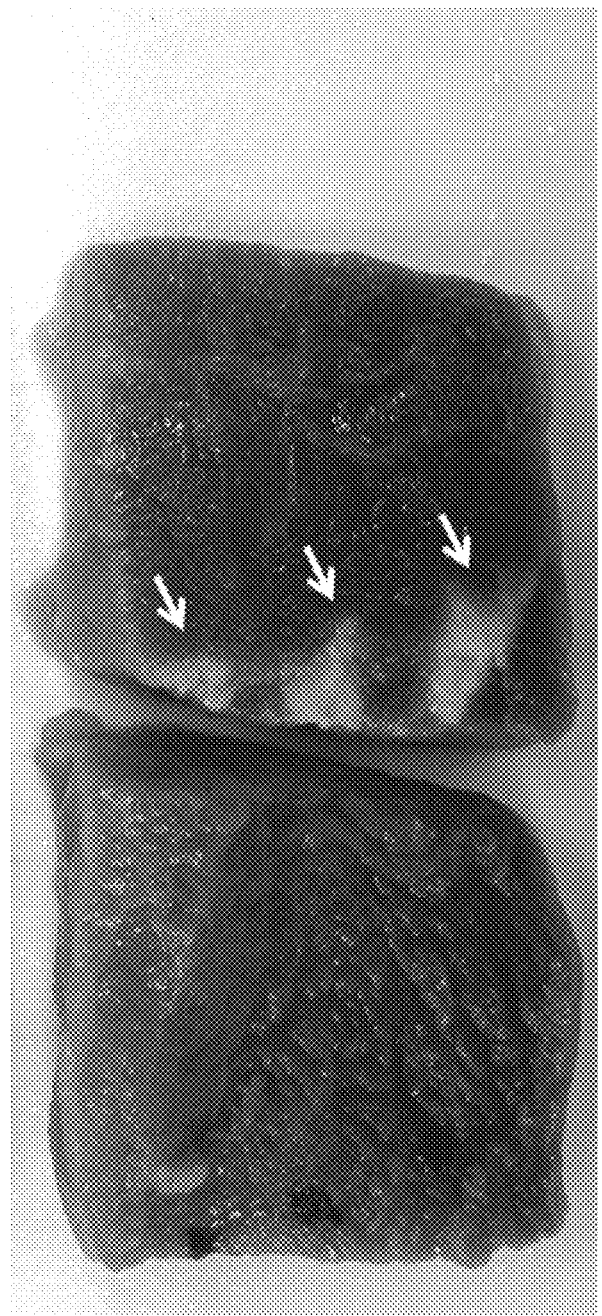
FIG. 5 shows the result of ex-vivo ablation experiment.

FIG. 5 shows that only pork is ablated as the distance between the HIFU hot spot and the fat is 5 mm or 10 mm. The HIFU dose is 510 W/10 seconds for three ablations.

Figure 6B:
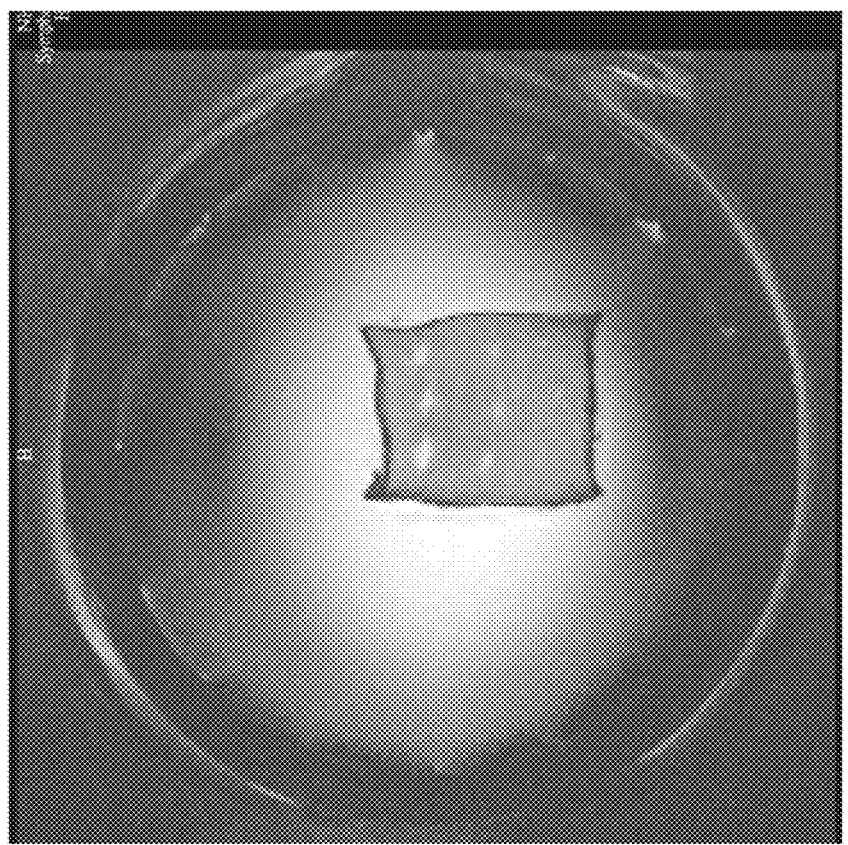
FIG. 6A-6B show the results of ex-vivo ablation experiments.
Figure 6A:

The ablated area is estimated by IR image (AI) and the photo of transverses slice of pork (AP), respectively as shown in FIG. 6A and FIG. 6B. FIG. 6A shows that the coronal-view photo of the pork slice post the HIFU sonication of 9 positions and FIG. 6B shows the coronal-view IR image of the same pork slice as FIG. 6A. As the results, seven lesions are observed, and their corresponding HIFU dose is 8, 10, 12, 14, 16, 18 and 20 seconds at the same input power of 430 W.

Figure 7:
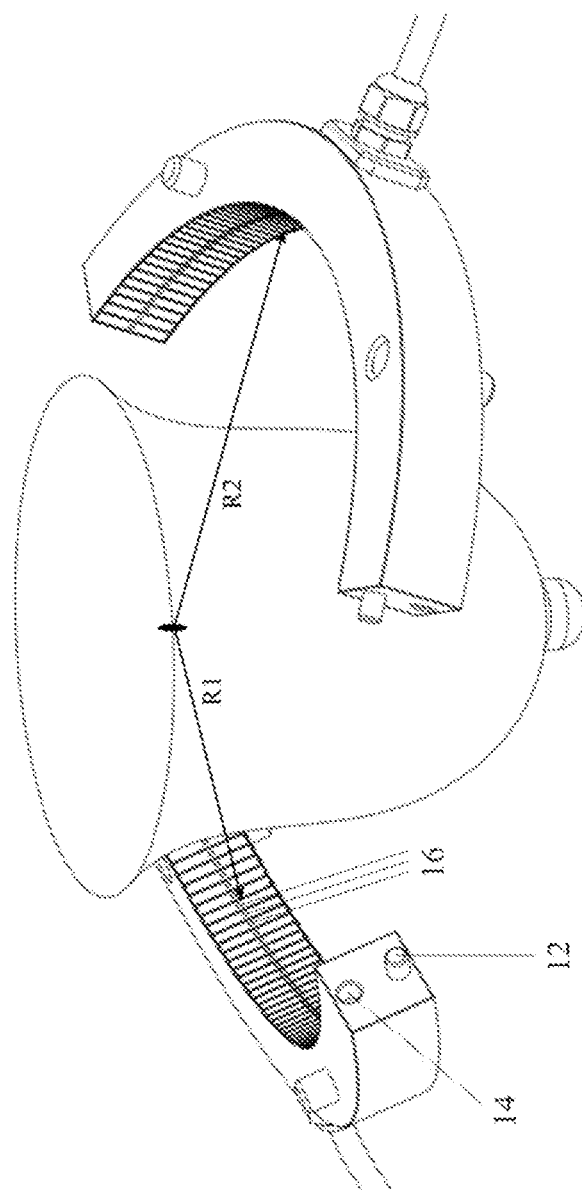
FIG. 7 shows the second embodiment of the arc ultrasonic transducer of the present invention.

Embodiment 2. The Therapeutic Ultrasonic Device Used in the Tissue Near Pectoralis Major Muscle Referring to FIG. 7, when the therapeutic ultrasonic device of the present invention is intended to treat the target tissue located near the pectoralis major muscle, two arc ultrasonic transducers are used. As shown in the figure, R stands the distance between the arc ultrasonic transducers and the ultrasonic focal zone of the pectoralis major muscle, and the two arc ultrasonic transducers may be disposed symmetrically or asymmetrically relative to the ultrasonic focal zone of the pectoralis major muscle, i.e., R1=R2 or R1≠R2. The two arc ultrasonic transducers can be controlled by rotation, displacement and phase adjustment via positioning device to form the focal zone accurately into the target tissue.

Embodiment 3. The Therapeutic Ultrasonic Device Used in Breast Tissue

Figure 8:
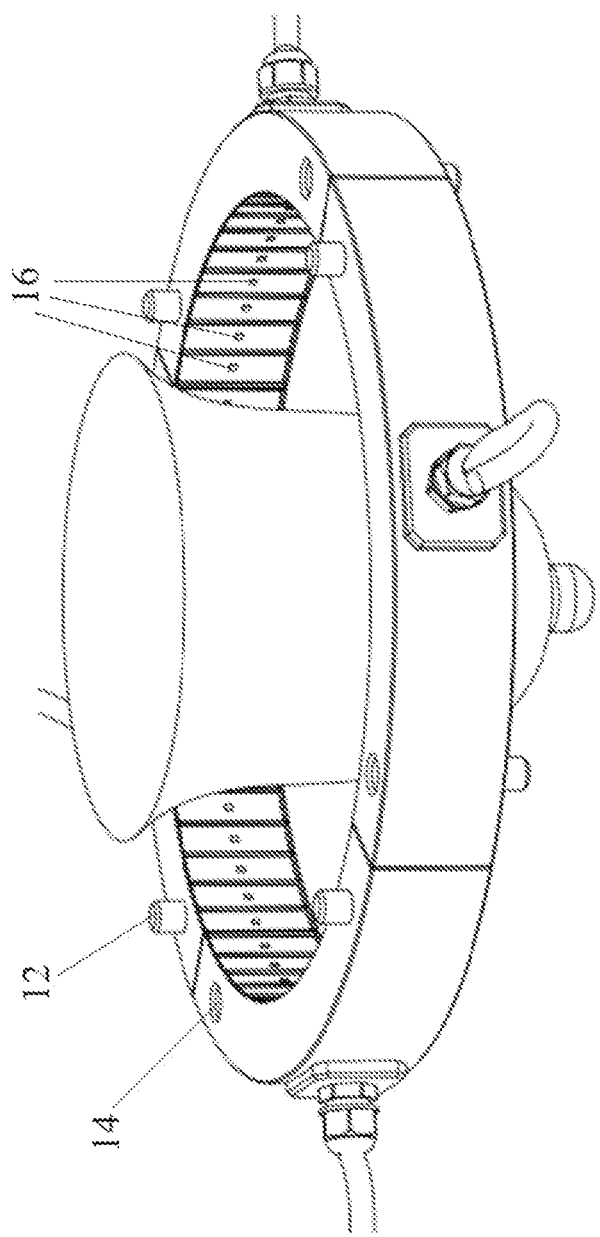
FIG. 8 shows the third embodiment of the ring-shaped ultrasonic transducer of the present invention.

Referring to FIG. 8, when the therapeutic ultrasonic device of the present invention is intended to treat the breast tissue, four arc ultrasonic transducers are used and assembled by the protruding part and concave part to form an ring-shaped ultrasonic transducer. As shown in the figure, the distance between each arc ultrasonic transducers of the ring-shaped ultrasonic transducer relative to the focal area of the target tissue are equal, i.e. R1=R2=R3=R4. And then moving the ultrasonic focal zone into to the target tissue through the positioning device.

Wherein the structural design of the ring-shaped ultrasonic transducer allows the acoustic radiation path to be scattered around the breast, so that the normal tissue at the front area of the radiation will only absorb low-intensity ultrasonic beams that do not cause skin or other normal tissue burns. In addition, the ring-shaped structure can be arranged in parallel with the sternum, so that the acoustic path and the sternum are almost parallel, thus the risk of sternum burn or normal tissue burn caused by direct radiation or reflection of the acoustic radiation is significantly reduced and improving the safety of high intensity focused ultrasound treatment. Further, the ring-shaped arranged piezoelectric vibrating parts are electrically controlled to concentrate ultrasonic beams dynamically so that the therapeutic ultrasonic device of the present invention can be used in treating tissue with millimeter size (mm-scale) and tissue with centimeter size (cm-scale) under single emission. Thus, the treatment time is effectively shorten.

Embodiment 4. The Therapeutic Ultrasonic Device Used in Central Nervous

Figure 9:
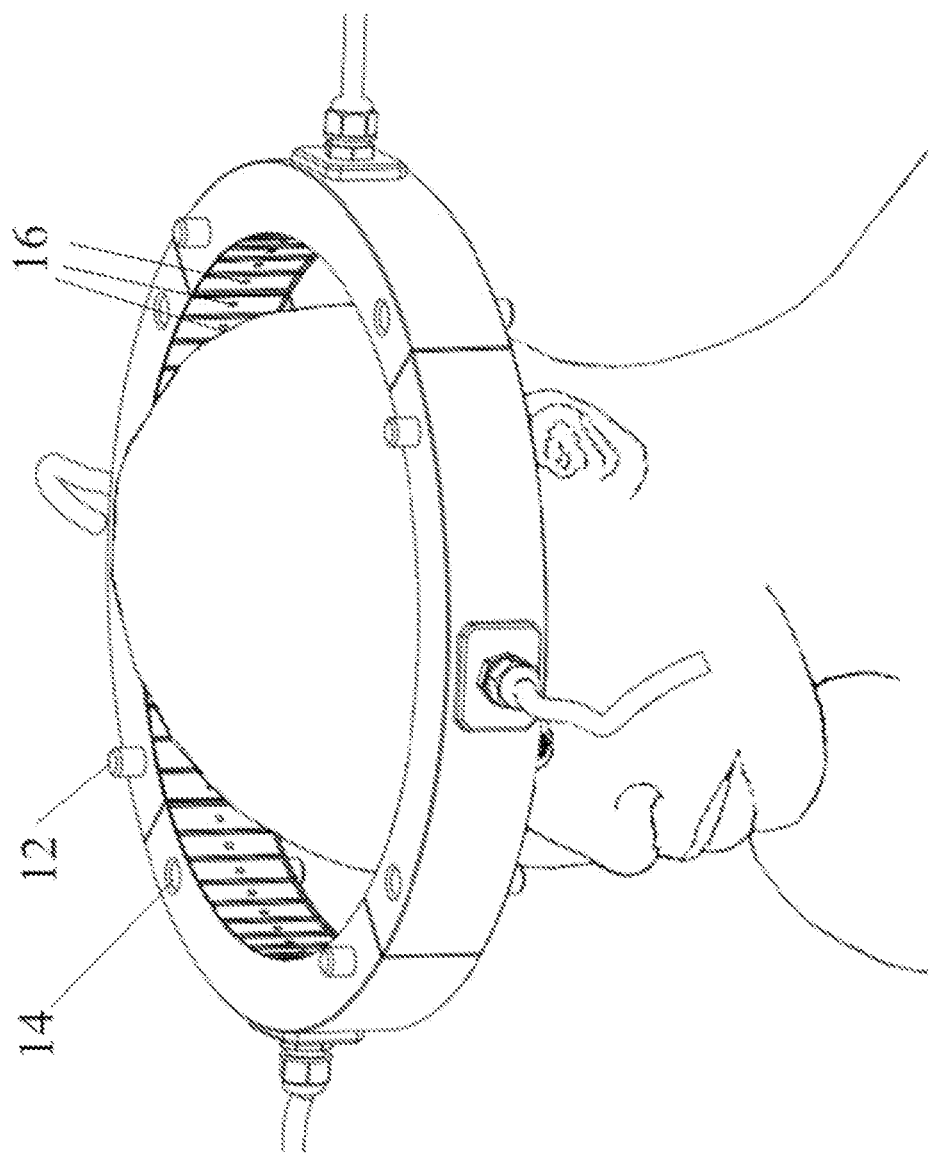
FIG. 9 shows the forth embodiment of the ring-shaped ultrasonic transducer of the present invention.

Please refers to FIG. 9, because brain tissue is protected by head skull, when the therapeutic ultrasonic device of the present invention is used for brain tissue, head skull will absorb and reflect lots of ultrasonic beams. In addition, non-uniformity of head skull tissue may increase the difficulty for concentrating ultrasonic beams. Accordingly, in the present embodiment, four arc ultrasonic transducers are assembled into a ring-shaped ultrasonic transducer. As shown in figure, the distance between each arc ultrasonic transducers of the ring-shaped ultrasonic transducer relative to the focal area of the target tissue are equal, i.e. R1=R2=R3=R4, and head will be surrounded by the ring-shaped ultrasonic transducer. So that, the irradiation and transmission path of the ultrasonic beams can be scattered around the skull, thereby reducing the energy intensity of the ultrasonic beams per unit area on the head and reducing the risk of burns in the skin, skull or other normal tissue.

To sum up, the problems and limitations of the prior art are solved by using the therapeutic ultrasonic device of the present invention based on the geometrical structure of the device and the ultrasonic beams control method of the device. In the part of the geometrical structure, one or more of the arc ultrasonic transducer(s) that can be used without being assembled, and a plurality of ultrasonic transducers can be assembled by joining the protruding part and the concave part to form the ring-shaped ultrasonic transducer or the cylindrical ultrasonic transducer. So that the arc ultrasonic transducers can be assembled at a suitable size for surrounding different body parts, solving the limitation of the prior art that single mode ultrasonic transducer cannot be widely used in various tissues. In addition, the ultrasonic beams are provided on the target tissue in a surrounded manner so that the energy of the ultrasonic beams is scattered in the body circumference in order to avoid excessive accumulation of energy at the front of the ultrasonic beams emission which cause non-target tissue burns. In the part of the ultrasonic beams control method of the device, the piezoelectric vibrating parts are combined with the piezoelectric sensing element to achieve dynamically focusing of ultrasonic beams during treatment and to form ultrasonic focal zones continuously and accurately at the target tissue for preventing burns of non-target tissue. Accordingly, the therapeutic ultrasonic device of the present invention does solve the technical difficulties and limitations of the current ultrasonic treatment in the clinical practice.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. A therapeutic ultrasonic device, comprising:
   more than one arc ultrasonic transducers that can be assembled,
   wherein each of the arc ultrasonic transducers comprises:
   a plurality of piezoelectric parts disposed at an inner side of the each arc ultrasonic transducer;
   a first protruding part and a first concave part disposed at one end of the each arc ultrasonic transducer; and
   a second protruding part and a second concave part disposed at another end of the each arc ultrasonic transducer,
   wherein the first protruding part and the first concave part of one arc ultrasonic transducer are coupled to the second concave part and the second protruding part of another of the arc ultrasonic transducer, respectively,
   wherein the plurality of piezoelectric parts further comprise a piezoelectric sensing element respectively;
   wherein the piezoelectric sensing element embedded in each of the piezoelectric parts are operated to receive an echo signal, each of the piezoelectric parts are configured to calculate a time lag from emission of ultrasonic beams to reflection of the echo signals, allowing for adjustment of a driving phase to concentrate the ultrasonic beams and forming of either a single ultrasonic focal zone or multiple ultrasonic focal zones.

2. The device of claim 1, wherein the more than one arc ultrasonic transducers are assembled into a ring-shaped ultrasonic transducer or an open cylindrical ultrasonic transducer.

3. The device of claim 2, wherein the protruding part assembles with the concave part to form the ring-shaped ultrasonic transducer or the open cylindrical ultrasonic transducer.

4. The device of claim 1, wherein the more than one arc ultrasonic transducers are phased array ultrasonic transducer.

5. The device of claim 1, wherein geometric parameters of the more than one arc ultrasonic transducers are radius of curvature R in a range of 5 to 25 cm, aperture diameter D in a range of 10 to 40 cm, and height H in a range of 1 to 3 cm.

6. A method for treating cancer by using the therapeutic ultrasonic device of claim 1, comprising propagating intensity focused ultrasound to a biological tissue for producing thermal effects and/or mechanical effects on the biological tissue.

7. The method of claim 6, wherein the therapeutic ultrasonic device induces cavitation in a microenvironment of the biological tissue to produce the mechanical effects.

8. The method of claim 6, wherein the thermal effects on the biological tissue leads to coagulative necrosis or cell death.

9. The method of claim 6, wherein the thermal effects and/or pressure on the biological tissue leads to cell activation, cell differentiation or cell regeneration.

10. The method of claim 6, wherein when the therapeutic ultrasonic device is used in breast tissue or brain tissue, four arc shaped ultrasonic transducers are assembled into a ring-shaped ultrasonic transducer.

* * * * *